United States Patent [19]
Briggs et al.

[11] Patent Number: 5,871,754
[45] Date of Patent: Feb. 16, 1999

[54] COSMETIC COMPOSITIONS

[75] Inventors: Gillian Scott Briggs, Egham; Teresa Barbara Crook, Camberley, both of England; Karen Fish, Berkshire, Great Britain; George Endel Deckner, Cincinnati, Ohio

[73] Assignee: The Procter & Gamble Company, Cincinnati, Ohio

[21] Appl. No.: 591,518

[22] PCT Filed: Aug. 1, 1994

[86] PCT No.: PCT/US94/08615

§ 371 Date: Jun. 27, 1996

§ 102(e) Date: Jun. 27, 1996

[87] PCT Pub. No.: WO95/04517

PCT Pub. Date: Feb. 16, 1995

[30] Foreign Application Priority Data

Aug. 6, 1993 [GB] United Kingdom .................. 9316322

[51] Int. Cl.$^6$ ...................................................... A61K 7/48
[52] U.S. Cl. ............................ 424/401; 424/69; 514/937; 514/938; 514/939
[58] Field of Search ................ 424/40, 69; 514/937–939

[56] References Cited

U.S. PATENT DOCUMENTS 4,147,782  4/1979  Klein et al. .............................. 424/230

FOREIGN PATENT DOCUMENTS 330369  8/1989  European Pat. Off. .

OTHER PUBLICATIONS

Harry's Cosmeticology by Ralph Harry, pp. 111–137 (1973).

*Primary Examiner*—Jyothsna Venkat
*Attorney, Agent, or Firm*—Darryl C. Little; George W. Allen; T. David Reed

[57] ABSTRACT

A make-up composition in the form of water-in-oil or oil-in-water emulsion comprising an acidic anti-active dissolved in the aqueous phase and a pigment or mixture of pigments dispersed in the oil phase. The make-up composition exhibits anti-effectiveness and product and color stability.

21 Claims, No Drawings

COSMETIC COMPOSITIONS

FIELD OF THE INVENTION

This application is a 371 of PCT/US 94/08615, filed on Aug. 1, 1994.

The present invention relates to cosmetic compositions and more particularly, to pigmented foundation make-up compositions and concealers having anti-acne activity and formulation and colour stability.

BACKGROUND OF THE INVENTION

A foundation composition can be applied to the face and other parts of the body to even skin tone and texture and to hide pores, imperfections, fine lines and the like. A foundation composition is also applied to moisturize the skin, to balance the oil level of the skin and to provide protection against the adverse effects of sunlight, wind and the harsh environment.

Make-up compositions are generally available in the form of liquid or cream suspensions, emulsions, gels, pressed powders or anhydrous oil and wax compositions.

U.S. Pat. No. 3,444,291 discloses a method of filling and camouflaging skin cavities by applying a composition which includes 65 to 75 parts by weight of a microcrystalline wax and about 25 to 35 parts of a mineral oil. The composition includes a colourant, preferably a coal tar dye, for example, D&C Red No. 17, which matches the colour of the user's skin.

A spreadable, flowable and greaseless cosmetic cover-up composition is taught in U.S. Pat. No. 4,486,405. That composition is characterized by the presence of a first and a second alkoxylated surfactant present in substantially the same concentration.

U.S. Pat. No. 4,804,532 recites a facial cosmetic powder which utilizes crystalline silica in much lower concentration than that employed in the then prior art compositions. This powder, used as a blush or a facial coating, is said to be effective in hiding skin wrinkles, lines and pores. The composition is a mixture of a colour phase and a diluent phase. The colour phase is formed by blending crystalline silica with colourants. The resultant colour phase is mixed with the diluent phase, essentially formed from nacreous materials such as talc and mica, to form the composition.

The use of a foundation composition which has a significantly high concentration of nacreous material is taught in U.S. Pat. No. 3,978,207. This foundation, a pressed powder composition, is characterized by the presence of a nacreous material such as mica and a binder oil which provides a frosted pearl effect, that is, a lustrous look. The colour of this foundation is provided by the nacreous material.

U.S. Pat. No. 4,659,562 discloses a cosmetic make-up composition which includes, as a binding agent therefore, an intimate mixture of from 5 to 95 weight percent of a mixture of finely divided silica and about 5 to 95 weight percent of finely divided polyethylene fibres. The composition is recited to maintain its uniformity over the areas of the skin to which it is applied. That is, it is said to be "creaseproof". The composition of the '562 patent includes colourant in admixture with nacreous agents.

Nakamura et al., Preprints of the XIVth I.F.S.C.C. Congress, Barcelona, 1986, Vol. I, 51–63 (1986) describes a novel make-up composition utilizing spherical silica and polydimethyl siloxane. This combination is recited to provide a foundation which reduces wrinkle visibility to a greater extent than make-up foundations with which it was compared. This reduction in wrinkle visibility is caused by optical blurring enhanced by the novel use of spherical silica and polydimethyl siloxane.

U.S. Pat. No. 5,143,722 discloses a cosmetic make-up composition comprising water-in-oil emulsions comprising pigment coated with polysiloxane, a silicone phase, a water phase and a polydiorganosiloxane-polyoxyalkylene copolymeric surfactant.

Foundations in the form of water-in-oil emulsions are well known and provide good coverage and good skin feel, wear and appearance. At the same time, it would be desirable to provide a foundation composition having topical anti-acne activity. There are many compounds which are known to exhibit anti-acne properties when applied topically to the skin. A commonly used keratolytic agent having anti-acne activity is salicylic acid. As salicylic acid is virtually insoluble in water it is difficult to incorporate into the aqueous phase of an emulsion composition. Delivery of salicylic acid from the pigment-containing oil phase of an emulsion foundation composition can, however, lead to discolouration of the composition due to interaction between the salicylic acid and pigments, especially of the iron oxide type. It would therefore be desirable to deliver the salicylic acid in soluble form from the aqueous phase.

Polyvinylpyrrolidone is known for use as a solubilizing/complexing agent in a variety of compositions.

GB-A-2,041,963 discloses an aqueous detergent composition for cleansing oily skin comprising a water-soluble salt of an N-acyl ester of sarcosine, a polyvinylpyrrolidone cosolubilizer and a protein and/or protein hydrolysate. The composition can also contain salicylic acid as a keratolytic agent and a buffer such as citric acid/citrate. There is no disclosure, however, of cosmetic compositions containing solubilized acidic anti-acne actives in fully protonated form as specified herein.

Since acidic anti-acne agents are most active at low pH (when a high concentration of free acid is present in solution) it would be desirable to deliver the agent from an aqueous phase at a pH at which it exists significantly in protonated form. It is accordingly a primary object of this invention to provide a cosmetic composition comprising a low pH aqueous solution of an anti-acne active.

It is also an object of the invention to provide a cosmetic composition having improved anti-acne activity and stability.

It is a further object of the invention to provide a cosmetic composition in the form of an oil-in-water or water-in-oil emulsion having improved colour stability and pigment/anti-acne active compatibility.

SUMMARY OF THE INVENTION

In accordance with one aspect of the present invention, there is provided a cosmetic composition in the form of an emulsion, gel or lotion comprising an aqueous/alcoholic solution of an acidic anti-acne active and a pyrrolidone-based complexing agent therefor, and wherein the aqueous/alcoholic solution has a pH of less than about $pK_a+1$, where $pK_a$ is the logarithmic acidity constant for the fully protonated anti-acne active.

The cosmetic compositions of the present invention provide anti-acne efficacy together with improved product and colour stability.

According to another aspect of the present invention there is provided a make-up composition in the form of a water-in-oil or oil-in-water emulsion comprising an acidic anti-acne active dissolved in the aqueous phase and a pigment or mixture of pigments dispersed in the oil phase.

All levels and ratios are by weight of total composition, unless otherwise indicated. Chain length and degrees of alkoxylation are also specified on a weight average basis.

DETAILED DESCRIPTION OF THE INVENTION

The cosmetic composition according to one aspect of the present invention comprises an aqueous/alcoholic solution of an acidic anti-acne active and a pyrrolidone-based complexing agent. The composition is in the form of an emulsion, gel or lotion.

According to this first aspect of the present invention a first essential component is an aqueous/alcoholic solution of an anti-acne active. Suitable anti-acne actives for use herein include salicylic acid, retinoic acid and its derivatives, azelaic acid and its derivatives, lactic acid, glycolic acid, pyruvic acid, flavonoids, and mixtures thereof.

The anti-acne active used in the composition herein is preferably selected from salicylic acid and azelaic acid, and mixtures thereof, more preferably salicyclic acid. The anti-acne active is present at a level of from about 0.1% to about 10%, preferably from about 0.1% to about 5%, more preferably from about 0.5% to about 3%, by weight of composition.

The anti-acne active is solubilized in water or an alcoholic solution, for example, solutions based upon $C_2$–$C_6$ alcohols, diols and polyols, preferred alcohols being selected from ethanol, dipropylene glycol, butylene glycol, hexylene glycol, and mixtures thereof. Alcohol is preferably present in the compositions herein at a level of from about 1% to about 20%. The final aqueous/alcoholic anti-acne active solution preferably has a pH at ambient temperature (25° C.) of less than about $pK_a+1$, where $pK_a$ is the logarithmic acidity constant for the fully protonated anti-acne active. In preferred embodiments, the pH of the final solution is less than about $pK_a$.

The logarithmic acidity constant is thus defined by reference to the equilibrium $$H^+ + H_{n-1}A = H_nA$$

where $H_nA$ is the fully protonated acid, n is the number of protons in the fully protonated acid and $H_{n-1}A$ is the conjugate base of the acid corresponding to loss of one proton.

The acidity constant for this equilibrium is therefore $$K_n = \frac{[H_nA]}{[H^+][H_{n-1}A]}$$

and $$pK_a = \log_{10} K_n$$

For the purposes of this specification, acidity constants are defined at 25° C. and at zero ionic strength. Literature values are taken where possible (see Stability Constants of Metal-Ion Complexes, Special Publication No. 25, The Chemical Society, London); where doubt arises they are determined by potentiometric titration using a glass electrode.

The $pK_a$ of the acidic anti-acne active used herein is preferably in the range of from about 1 to about 6, more preferably from about 1 to about 4.5, especially from about 1.5 to about 4.0.

The pH of the final aqueous/alcoholic anti-acne active solution is preferably in the range of from about 1 to about 7, more preferably from about 2 to about 5, especially from about 2 to about 4. At pH values of less than about 5 the aqueous phase is preferably free of acid labile species such as acrylic acid/ethyl acrylate copolymers and polyglycerylmethacrylate.

A second essential component of the compositions of the first aspect of the present invention is a pyrrolidone-based complexing agent.

The pyrrolidone-based complexing agent is useful herein from the viewpoint of aiding solubilization of the anti-acne active. The pyrrolidone-based complexing agent used herein is preferably selected from polyvinylpyrrolidone complexing agents or $C_1$–$C_4$ alkyl polyvinylpyrrolidone complexing agents having a molecular weight (viscosity average) in the range from about 1500 to about 1,500,000, preferably from about 3000 to about 700,000, more preferably from about 5000 to about 100,000. Suitable examples of pyrrolidone-based complexing agents are polyvinylpyrrolidone (PVP) (or povidone) and butylated polyvinylpyrrolidone. The most preferred pyrrolidone-based complexing agent herein is a polyvinylpyrrolidone complexing agent. PVP is commercially available under the trade name Luviskol (RTM) from BASF. A preferred PVP complexing agent herein is Luviskol K17 which has a viscosity-average molecular weight of about 9,000. Other pyrrolidone-based complexing agents for use herein include $C_1$–$C_{18}$ alkyl or hydroxyalkyl pyrrolidones such as lauryl pyrrolidone.

The pyrrolidone-based complexing agent is present in the composition herein in a level of from about 0.1% to about 10%, preferably from about 0.1% to about 5% by weight of composition. The weight ratio of anti-acne active:pyrrolidone-based complexing agent is in the range from about 10:1 to about 1:10, preferably from about 5:1 to about 1:5.

Preferred embodiments of the invention additionally comprise from about 0.01% to about 5% by weight of an acid or salt thereof which is soluble in water at pH values of less than or equal to the $pK_a$ of the corresponding acid, for example, an acid selected from citric acid, boric acid, and salts, and mixtures thereof. These materials are valuable herein in combination with the pyrrolidone-based complexing agent from the viewpoint of aiding solubilization of the anti-acne active. Particularly preferred herein from this viewpoint is a sodium salt of citric acid. In preferred embodiments, the acid or salt thereof is soluble to a level of at least 5% w/w at 25° C.

The composition of the present invention can be in emulsion (w/o or o/w), gel or lotion form but is preferably in the form of a water-in-oil emulsion, wherein in preferred embodiments the oil phase comprises a mixture of volatile silicones and non-volatile silicones. The silicone oil is present in an amount of from about 1% to about 50% by weight. Suitable volatile silicone oils include cyclic and linear volatile polyorganosiloxanes (as used herein, "volatile" refers to those materials which have a measurable vapour pressure at ambient conditions).

A description of various volatile silicones is found in Todd, et al.. "Volatile Silicone Fluids for Cosmetics", 91 *Cosmetics and Toiletries* 27–32 (1976).

Preferred cyclic silicones include polydimethylsiloxanes containing from about 3 to about 9 silicon atoms, preferably containing from about 4 to about 5 silicon atoms. Preferred linear silicone oils include the polydimethylsiloxanes containing from about 3 to about 9 silicon atoms. The linear volatile silicones generally have viscosities of less than about 5 centistokes at 25° C., while the cyclic materials have viscosities of less than about 10 centistokes. Examples of silicone oils useful in the present invention include: Dow Corning 344, Dow Corning 21330, Dow Corning 345, and Dow Corning 200 (manufactured by the Dow Corning Corporation): Silicone 7207 and Silicone 7158 (manufactured by the Union Carbide Corporation). SF:202 (manufactured by General Electric) and SWS-03314 (manufactured by Stauffer Chemical).

Suitable non-volatile silicones preferably have an average viscosity of from about 1,000 to about 2,000,000 mm$^2$.s$^{-1}$ at 25° C. more preferably from about 10,000 to about 1,800,000 mm$^2$.s$^{-1}$, even more preferably from about 100,000 to about 1,500,000 mm$^2$.s$^{-1}$. Lower viscosity non-volatile silicone conditioning agents, however, can also be used. Viscosity can be measured by means of a glass capillary viscometer as set forth in Dow Corning Corporate Test Method CTM0004, Jul. 20, 1970. Suitable non-volatile silicone fluids for use herein include polyalkyl siloxanes, polyaryl siloxanes, polyalkylaryl siloxanes, polysiloxanes with amino functional substitutions, polyether siloxane copolymers, and mixtures thereof. The siloxanes useful in the present invention may be endcapped with any number of moieties, including, for example, methyl, hydroxyl, ethylene oxide, propylene oxide, amino and carboxyl. However, other silicone fluids having skin conditioning properties may be used. The non-volatile polyalkyl siloxane fluids that may be used include, for example, polydimethylsiloxanes. These siloxanes are available, for example, from the General Electric Company as a Viscasil (RTM) series and from Dow Corning as the Dow Corning 200 series. Preferably, the viscosity ranges from about 10 mm$^2$.s$^{-1}$ to about 100,000 mm$^2$.s$^{-1}$ at 25° C. The polyalkylaryl siloxane fluids that may be used, also include, for example, polymethylphenylsiloxanes. These siloxanes are available, for example, from the General Electric Company as SF 1075 methyl phenyl fluid or from Dow Corning as 556 Cosmetic Grade Fluid. The polyether siloxane copolymer that may be used includes, for example, a polypropylene oxide modified dimethylpolysiloxane (e.g., Dow Corning DC-1248) although ethylene oxide or mixtures of ethylene oxide and propylene oxide may also be used.

References disclosing suitable silicone fluids include U.S. Pat. No. 2,826,551, Green; U.S. Pat. No. 3,964,500, Drakoff, issued Jun. 22nd, 1976; U.S. Pat. No. 4,364,837, Pader; and GB-A-849,433, Woolston. In addition, *Silicone Compounds* distributed by Petrarch Systems Inc., 1984 provides an extensive (though not exclusive) listing of suitable silicone fluids.

Preferred non-volatile silicones for use herein include polydiorganosiloxane-polyoxyalkylene copolymers containing at least one polydiorganosiloxane segment and at least one polyoxyalkylene segment, said polydiorganosiloxane segment consisting essentially of

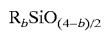

siloxane units wherein b has a value of from about 0 to about 3, inclusive, there being an average value of approximately 2 R radicals per silicon for all siloxane units in the copolymer, and R denotes a radical selected from methyl, ethyl, vinyl, phenyl and a divalent radical bonding said polyoxyalkylene segment to the polydiorganosiloxane segment, at least about 95% of all R radicals being methyl; and said polyoxyalkylene segment having an average molecular weight of at least about 1000 and consisting of from about 0 to about 50 mol percent polyoxypropylene units and from about 50 to about 100 mol percent polyoxyethylene units, at least one terminal portion of said polyoxyalkylene segment being bonded to said polydiorganosiloxane segment, any terminal portion of said polyoxyalkylene segment not bonded to said polydiorganosiloxane segment being satisfied by a terminating radical; the weight ratio of polydiorganosiloxane segments to polyoxyalkylene segments in said copolymer having a value of from about 2 to about 8. Such polymers are described in U.S. Pat. No. 4,268,499.

More preferred for use herein are polydiorganosiloxane-polyoxyalkylene copolymers having the general formula:

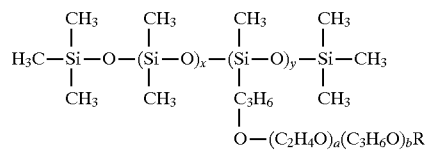

wherein x and y are selected such that the weight ratio of polydiorganosiloxane segments to polyoxalkylene segments is from about 2 to about 8, the mol ratio of a:(a+b) is from about 0.5 to about 1, and R is a chain terminating group, especially selected from hydrogen; hydroxyl; alkyl, such as methyl, ethyl, propyl, butyl, benzyl; aryl, such as phenyl; alkoxy such as methoxy, ethoxy, propoxy, butoxy; benzyloxy; aryloxy, such as phenoxy; alkenyloxy, such as vinyloxy and allyloxy; acyloxy, such as acetoxy, acryloxy and propionoxy and amino, such as dimethylamino.

The number of and average molecular weights of the segments in the copolymer are such that the weight ratio of polydiorganosiloxane segments to polyoxyalkylene segments in the copolymer is preferably from about 2.5 to about 4.0.

Suitable copolymers are available commercially under the tradenames Belsil (RTM) from Wacker-Chemie GmbH, Geschaftsbereich S, Postfach D-8000 Munich 22 and Abil (RTM) from Th. Goldschmidt Ltd,. Tego House, Victoria Road, Ruislip, Middlesex, HA4 OYL. Particularly preferred for use herein are Belsil (RTM) 6031, Abil (RTM) B88183 and DC3225C. A preferred silicone herein is known by its CTFA designation as dimethicone copolyol.

The silicone oil phase preferably comprises from about 2% to about 25%, more preferably from about 5% to about 15% by weight of composition of non-volatile silicones.

A highly preferred component of the compositions herein is a humectant or mixture of humectants. The humectant or mixture of humectants herein is present in an amount of from about 0.1% to about 30% preferably from about 5% to about 25%, and more preferably from about 10% to about 20% by weight of composition. Suitable humectants are selected from glycerine and polyglycerylmethacrylate lubricant having a viscosity at 25° C. of 300,000 to 1,100,000 cps; a specific gravity at 25° C. of 1 to 1.2 g/ml, a pH of 5.0 to 5.5; a bound water content of 33 to 58%; and, a free water content from 5 to 20%.

The humectant can be incorporated at least partly into the oil phase of the water-in-oil emulsion so as to form a multiphase humectant-in-oil-in-water dispersion. The oil phase preferably comprises from about 0.1% to about 10%, more preferably from about 0.1% to about 3% by weight of humectant on a composition basis. The humectant can be introduced into the oil phase in the form of a mixture with or incorporated within a particulate lipophilic or hydrophobic carrier material.

Polyglycerylmethacrylate lubricants having the desired properties are marketed by Guardian Chemical Corporation under the trademark "Lubrajel". The "Lubrajels" identified as "Lubrajel DV", "Lubrajel MS", and "Lubrajel CG" are preferred in the present invention. The gelling agents sold under these trademarks contain about 1% propylene glycol.

Other suitable humectants include sorbitol, panthenols, propylene glycol, butylene glycol, hexylene glycol, alkoxylated glucose derivatives, such as Glucam (RTM) E-20, hexanetriol, and glucose ethers, and mixtures thereof. Urea is also suitably added as a humectant in the internal aqueous phase.

The panthenol moisturiser can be selected from D-panthenol ([R]-2,4-dihydroxy-N-[3-hydroxypropyl)]-3,3-dimethylbutamide), DL-panthenol, calcium pantothenate, royal jelly, panthetine, pantotheine, panthenyl ethyl ether, pangamic acid, pyridoxin, pantoyl lactose and Vitamin B complex.

The preferred humectant herein is glycerine. Chemically, glycerine is 1,2,3-propanetriol and is a product of commerce.

Preferred embodiments herein comprise a pigment or mixture of pigments. Suitable pigments for use herein can be inorganic and/or organic. Also included within the term pigment are materials having a low colour or lustre such as matte finishing agents, and also light scattering agents. Examples of suitable pigments are iron oxides, acyl-glutamate iron oxides, ultramarine blue, D&C dyes, carmine, and mixtures thereof. Depending upon the type of make-up composition, eg. foundation or blusher, a mixture of pigments will normally be used.

It is a feature of the composition herein that the pigment and anti-acne active have excellent overall compatability and colour stability. Thus according to another aspect of the present invention there is provided a make-up composition in the form of a water-in-oil or oil-in-water emulsion comprising an acidic anti-acne active dissolved in the aqueous phase and a pigment or mixture of pigments dispersed in the oil phase.

The foundation composition can also include at least one matte finishing agent. The function of the matte finishing agent is to hide skin defects and reduce shine. Such cosmetically acceptable inorganic agents, i.e., those included in the CTFA Cosmetic Ingredient Dictionary, Third Ed., as silica, hydrated silica, silicone-treated silica beads, mica, talc, polyethylene, titanium dioxide, bentonite, hectorite, kaolin, chalk, diatomaceous earth, attapulgite zinc oxide and the like may be utilized. Of particular usefulness as a matte finishing agent is low lustre pigment such as titanated mica (mica coated with titanium dioxide) coated with barium sulfate. Of the inorganic components useful as a matte finishing agent low lustre pigment, talc, polyethylene, hydrated silica, kaolin, titanium dioxide and mixtures thereof are particularly preferred. Materials suitable for use herein as light-scattering agents can be generally described as spherical shaped inorganic materials having a particle size of up to about 100 microns, preferably from about 5 to about 50 microns, for example spherical silica particles.

The total concentration of the pigment may be from about 0.1 to about 25% by weight and is preferably from about 1 to about 10% by weight of the total composition, the exact concentration being dependent to some extent upon the specific mixture of pigments selected for use in a foundation make-up or blusher to achieve the desired shades. The preferred compositions contain from about 2% to about 20% by weight of titanium dioxide and most preferably from about 5% to about 10% by weight of titanium dioxide.

The preferred pigments for use herein from the viewpoint of moisturisation, skin feel, skin appearance and emulsion compatibility are treated pigments. The pigments can be treated with compounds such as amino acids such as lysine, silicones, lauroyl, collagen, polyethylene, lecithin and ester oils. The more preferred pigments are the silicone (polysiloxane) treated pigments.

The balance of the composition of the present invention is deionized water. The composition preferably comprises from about 30% to about 95%, more preferably from about 40% to about 80% by weight of the oil phase, and from about 5% to about 70%, more preferably from about 20% to about 60% by weight of the water phase.

The make-up compositions of the present invention can also comprise a particulate cross-linked hydrophobic acrylate or methacrylate copolymer. This copolymer is particularly valuable for reducing shine and controlling oil while helping to provide effective moisturization benefits. The cross-linked hydrophobic polymer is preferably in the form of a copolymer lattice with at least one active ingredient dispersed uniformly throughout and entrapped within the copolymer lattice. Alternatively, the hydrophobic polymer can take the form of a porous particle having a surface area ($N_2$-BET) in the range from about 50 to 500, preferably 100 to 300 $m^2/g$ and having the active ingredient absorbed therein.

The cross-linked hydrophobic polymer when used herein is in an amount of from about 0.1% to about 10% by weight and is preferably incorporated in the external silicone-containing oil phase. The active ingredient can be one or more or a mixture of skin compatible oils, skin compatible humectants, emollients, moisturizing agents and sunscreens. The polymer material is in the form of a powder, the powder being a combined system of particles. The system of powder particles forms a lattice which includes unit particles of less than about one micron in average diameter, agglomerates of fused unit particles of sized in the range of about 20 to 100 microns in average diameter and aggregates of clusters of fused agglomerates of sizes in the range of about 200 to 1,200 microns in average diameter.

The powder material of the present invention which can be employed as the carrier for the active ingredient can be broadly described as a cross-linked "post absorbed" hydrophobic polymer lattice. The powder preferably has entrapped and dispersed therein, an active which may be in the form of a solid, liquid or gas. The lattice is in particulate form and constitutes free flowing discrete solid particles when loaded with the active material. The lattice may contain a predetermined quantity of the active material. The polymer has the structural formula:

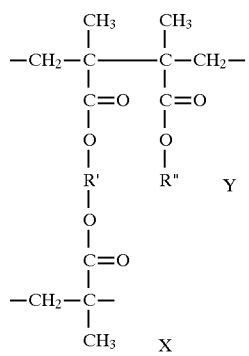

where the ratio of x to y is 80:20, R' is —$CH_2CH_2$— and R" is —$(CH_2)_{11}CH_3$.

The hydrophobic polymer is a highly crosslinked polymer, more particularly a highly cross-linked polymethacrylate copolymer. The material is manufactured by the Dow Corning Corporation, Midland. Mich., USA, and sold under the trademark POLYTRAP (RTM). It is an ultralight free-flowing white powder and the particles are capable of absorbing high levels of lipophilic liquids and some hydrophilic liquids while at the same time maintaining a free-flowing powder character. The powder structure consists of a lattice of unit particles less than one micron that are fused into agglomerates of 20 to 100 microns and the agglomerates are loosely clustered into macro-particles or aggregates of about 200 to about 1200 micron size. The polymer powder is capable of containing as much as four times its weight of fluids, emulsions, dispersions or melted solids.

Adsorption of actives onto the polymer powder can be accomplished using a stainless steel mixing bowl and a spoon, wherein the active is added to the powder and the spoon is used to gently fold the active into the polymer powder. Low viscosity fluids may be adsorbed by addition of the fluids to a sealable vessel containing the polymer and then tumbling the materials until a consistency is achieved. More elaborate blending equipment such as ribbon or twin cone blenders can also be employed. The preferred active ingredient for use herein is glycerine. Preferably, the weight ratio of humectant: carrier is from about 1:4 to about 3:1.

Also suitable as a highly cross-linked polymethacrylate copolymer is Microsponges 5647. This takes the form of generally spherical particles of cross-linked hydrophobic polymer having a pore size of from about 0.01 to about 0.05 $\mu$m and a surface area of 200–300 m$^2$/g. Again, it is preferably loaded with humectant in the levels described above.

The compositions of the invention can also contain a hydrophilic gelling agent at a level preferably from about 0.01% to about 10%, more preferably from about 0.02% to about 2%, and especially from about 0.02% to about 0.5%. The gelling agent preferably has a viscosity (1% aqueous solution, 20° C., Brookfield RVT) of at least about 4000 mPa.s, more preferably at least about 10,000 mPa.s and especially at least 50,000 mPa.s.

Suitable hydrophilic gelling agents can generally be described as water-soluble or colloidally water-soluble polymers, and include cellulose ethers (e.g. hydroxyethyl cellulose, methyl cellulose, hydroxypropylmethyl cellulose), polyvinylalcohol, polyquaternium-10, guar gum, hydroxypropyl guar gum and xanthan gum.

Among suitable hydrophilic gelling agents are acrylic acid/ethyl acrylate copolymers and the carboxyvinyl polymers sold by the B. F. Goodrich Company under the trademark of Carbopol resins. These resins consist essentially of a colloidally water-soluble polyalkenyl polyether crosslinked polymer of acrylic acid crosslinked with from 0.75% to 2.00% of a crosslinking agent such as for example polyallyl sucrose or polyallyl pentaerythritol. Examples include Carbopol 934, Carbopol 940, Carbopol 950, Carbopol 980, Carbopol 951 and Carbopol 981. Carbopol 934 is a water-soluble polymer of acrylic acid crosslinked with about 1% of a polyallyl ether of sucrose having an average of about 5.8 allyl groups for each sucrose molecule. Also suitable for use herein are hydrophobically-modified cross-linked polymers of acrylic acid having amphipathic properties available under the Trade Name Carbopol 1382, Carbopol 1342 and Pemulen TR-1 (CTFA Designation: Acrylates/10-30 Alkyl Acrylate Crosspolymer). A combination of the polyalkenyl polyether cross-linked acrylic acid polymer and the hydrophobically modified cross-linked acrylic acid polymer is also suitable for use herein. Other suitable gelling agents suitable for use herein are oleogels such as trihydroxystearin and aluminium magnesium hydroxy stearate. The gelling agents herein are particularly valuable for providing excellent stability characteristics over both normal and elevated temperatures.

Neutralizing agents suitable for use in neutralizing acidic group containing hydrophilic gelling agents herein include sodium hydroxide, potassium hydroxide, ammonium hydroxide, monoethanolamine, diethanolamine and triethanolamine.

The make-up compositions herein can additionally comprise an emollient. Emollients suitable for the compositions of the present invention include natural and synthetic oils selected from mineral, vegetable, and animal oils, fats and waxes, fatty acid esters, fatty alcohols, alkylene glycol and polyalkylene glycol ethers and esters, fatty acids and mixtures thereof.

Suitable emollients for use herein include, for example, optionally hydroxy-substituted $C_8$–$C_{50}$ unsaturated fatty acids and esters thereof, $C_1$–$C_{24}$ esters of $C_8$–$C_{30}$ saturated fatty acids such as isopropyl myristate, cetyl palmitate and octyldodecylmyristate (Wickenol 142), beeswax, saturated and unsaturated fatty alcohols such as behenyl alcohol and cetyl alcohol, hydrocarbons such as mineral oils, petrolatum and squalane, fatty sorbitan esters (see U.S. Pat. No. 3,988,255, Seiden, issued Oct. 26, 1976), lanolin and lanolin derivatives, such as lanolin alcohol ethoxylated, hydroxylated and acetylated lanolins, cholesterol and derivatives thereof, animal and vegetable triglycerides such as almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grapeseed oil, and sunflower seed oil and $C_1$–$C_{24}$ esters of dimer and trimer acids such as diisopropyl dimerate, diisostearylmalate, diisostearyldimerate and triisostearyltrimerate.

Preferred emollients are selected from hydrocarbons such as isohexadecane, mineral oils, petrolatum and squalane, lanolin alcohol, and stearyl alcohol. These emollients may be used independently or in mixtures and may be present in the composition of the present invention in an amount from about 1% to about 30% by weight, and preferably are present in an amount from about 5% to about 15% by weight of the total composition.

The composition may also contain additional materials such as, for example, fragrances, fillers such as nylon, sun-screens, preservatives, electrolytes such as sodium chloride, proteins, antioxidants, chelating agents and water-in-oil emulsifiers as appropriate.

Another optional component of the make-up composition is one or more ultraviolet absorbing agents. Ultraviolet absorbing agents, often described as sunscreening agents, can be present in a concentration in the range of between about 1% and about 12% by weight, based on the total weight of composition. Preferably, the UV absorbing agents constitute between about 2% and 8% by weight. More preferably, the UV absorbing agents can be present in the composition in a concentration range of between about 4% and about 6% by weight. Of the ultraviolet absorbing agents suitable for use herein, benzophenone-3, octyl dimethyl PABA (Padimate O) and mixtures thereof are particularly preferred.

Another optional but preferred component herein is one or more additional chelating agents, preferably in the range of from about 0.02% to about 0.10% by weight, based on the total weight of the composition. Preferably, the chelating agent is present in a concentration in the range of between about 0.03% and about 0.07% by weight, based on the total weight of the composition. Among the chelating agents that may be included in the composition is tetrasodium EDTA.

Another optional but preferred component of the foundation composition is one or more preservatives. The preservative concentration in the foundation composition, based on the total weight of that composition, is in the range of between about 0.05% and about 0.8% by weight, preferably between about 0.1% and about 0.3% by weight. Suitable preservatives for use herein include sodium benzoate and propyl paraben, and mixtures thereof.

The make-up compositions of the present invention can be in the form of foundations, blushers, concealers, compact powders, and the like, preferably as foundations and concealers.

The following Table is provided to illustrate compositions of the make-up of the present invention:

| Example | I Wt % | II Wt % | III Wt % | IV Wt % | V Wt % | VI Wt % | VII Wt % |
|---|---|---|---|---|---|---|---|
| A. | | | | | | | |
| Cetyloctanoate | 2.00 | 0.0 | 0.0 | 0.0 | 0.0 | 0.0 | 2.0 |
| Cyclomethicone | 8.57 | 12.25 | 12.25 | 15.0 | 12.0 | 8.57 | 8.57 |
| Cyclomethicone/dimethicone copolyol (90:10) | 17.16 | 20.0 | 20.0 | 5.0 | 8.0 | 10.0 | 17.16 |
| Propylparaben (33%) in laureth-7 | 0.75 | 0.75 | 0.0 | 0.75 | 0.0 | 0.75 | 0.75 |
| Dimethicone Fluid | 2.0 | 0.0 | 2.0 | 3.0 | 5.0 | 10.0 | 0.0 |
| Benzophenene-3 Propylene glycol | 0.0 | 0.0 | 0.0 | 0.0 | 0.0 | 2.0 | 0.0 |
| Dicaprylate/Dicaprate | 0.0 | 0.0 | 0.0 | 5.0 | 0.0 | 10.0 | 0.0 |
| B. | | | | | | | |
| Titanium Dioxide | 8.25 | 6.0 | 1.5 | 6.0 | 8.0 | 20.0 | 8.25 |
| Titanium Dioxide treated (Aluminium hydrate, stearic acid) | 0.25 | 0.5 | 3.0 | 0.25 | 0.25 | 0.0 | 0.25 |
| Titanated Micas | 0.1 | 0.1 | 0.1 | 0.25 | 1.0 | 0.0 | 0.1 |
| Talc | 3.38 | 4.5 | 6.0 | 0.7 | 0.7 | 0.7 | 3.38 |
| Silica | 0.6 | 4.25 | 6.0 | 4.25 | 0.6 | 0.6 | 0.6 |
| Nylon | 0.0 | 0.0 | 0.0 | 0.0 | 0.5 | 0.0 | 0.0 |
| C. | | | | | | | |
| Cyclomethicone/dimethicone copolyol (90:10) | 1.85 | 1.5 | 1.85 | 5.0 | 1.0 | 1.0 | 1.85 |
| D. | | | | | | | |
| Yellow Iron Oxide | 1.2 | 1.2 | 0.6 | 0.4 | 1.2 | 1.2 | 1.2 |
| Red Iron Oxide | 0.49 | 0.6 | 0.6 | 0.49 | 0.49 | 0.2 | 0.6 |
| Black Iron Oxide | 0.16 | 0.1 | 0.24 | 0.1 | 0.1 | 0.24 | 0.24 |
| Ultramarine Blue | 0.0 | 0.0 | 0.0 | 0.1 | 0.0 | 0.0 | 0.0 |
| Cyclomethicone | 0.0 | 0.0 | 0.0 | 0.0 | 0.68 | 0.0 | 0.0 |
| E. | | | | | | | |
| Synthetic Wax | 0.1 | 0.5 | 0.5 | 0.1 | 0.0 | 0.0 | 0.0 |
| Arachidyl behenate | 0.3 | 0.0 | 0.0 | 0.3 | 0.5 | 0.3 | 0.3 |
| Stearic Acid | 0.0 | 0.0 | 0.0 | 0.0 | 0.0 | 0.0 | 2.5 |
| Palmitic Acid | 0.0 | 0.0 | 0.0 | 0.0 | 0.0 | 2.5 | 0.0 |
| Silica (spheron P1500) | 6.0 | 0.0 | 6.0 | 0.0 | 0.0 | 0.0 | 0.0 |
| F. | | | | | | | |
| Trihydroxystearin | 0.3 | 0.3 | 1.5 | 1.5 | 0.0 | 0.0 | 0.0 |
| Cyclomethicone | 1.0 | 4.0 | 0.0 | 0.0 | 4.0 | 4.0 | 4.0 |
| Beeswax | 1.5 | 1.2 | 0.0 | 0.0 | 1.3 | 0.0 | 0.0 |
| Abil WED9 | 0.0 | 3.0 | 0.0 | 0.0 | 0.0 | 0.0 | 0.0 |
| G. | | | | | | | |
| Ethylene brassylate | 0.05 | 0.0 | 0.0 | 0.0 | 0.0 | 0.05 | 0.05 |
| BHT | 0.05 | 0.0 | 0.0 | 0.0 | 0.0 | 0.05 | 0.05 |
| H. | | | | | | | |
| Deionized water | | | | to 100 | | | |
| Ethanol | 6 | 5.5 | 4.0 | 7 | 6.0 | 8.0 | 6.0 |
| Salicylic acid | 1 | 1 | 1 | 2 | 2 | 2 | 0.0 |
| Azeleic acid | 0.0 | 0.0 | 0.0 | 0.0 | 0.0 | 0.0 | 0.0 |
| Propylene glycol | 2.37 | 2.37 | 1.37 | 2.37 | 0.0 | 2.37 | 0.0 |
| Dipropylene glycol | 6.0 | 5.0 | 6.5 | 7.00 | 8.0 | 6.0 | 5.0 |
| Sodium chloride | 0.5 | 0.5 | 0.5 | 0.5 | 0.5 | 0.5 | 1.0 |
| Glycerine | 4.5 | 5.0 | 10.0 | 5.0 | 5.0 | 10.0 | 15.0 |
| Tetrasodium EDTA | 0.05 | 0.05 | 0.05 | 0.1 | 0.1 | 0.1 | 0.01 |
| Triethanolamine | 0.0 | 0.0 | 0.0 | 0.0 | 0.0 | 0.0 | 0.75 |
| Allantoin | 0.0 | 0.0 | 0.1 | 0.0 | 0.0 | 0.0 | 0.0 |
| sunscreen | 0.0 | 0.0 | 0.0 | 0.2 | 0.2 | 0.0 | 0.0 |
| polyvinylpyrrolid-one (Luviskol K17) | 1 | 2 | 1.5 | 1 | 1 | 1 | 2 |
| Sodium citrate | 0.3 | 0.3 | 0.0 | 0.2 | 0.4 | 0.3 | 0.4 |
| Sodium Tetraborate | 0.0 | 0.0 | 0.1 | 0.4 | 0.0 | 0.2 | 0.0 |
| pH of aqueous phase | 2.9 | 2.8 | 2.9 | 3.2 | 3.0 | 2.9 | 3.1 |
| I. | | | | | | | |
| Deionized Water | 0.0 | 0.0 | 0.0 | 0.0 | 10.0 | 0.0 | 0.0 |
| J. | | | | | | | |
| Propylene Glycol | 0.0 | 0.0 | 0.0 | 2.0 | 0.0 | 0.0 | 0.0 |
| Xanthan Gum | 0.0 | 0.0 | 0.0 | 0.08 | 0.0 | 0.0 | 0.0 |
| K. | | | | | | | |
| Essential Oils | 0.0 | 0.0 | 0.0 | 0.20 | 0.0 | 0.0 | 0.0 |
| Perfume Oil | 0.0 | 0.25 | 0.0 | 0.20 | 0.0 | 0.0 | 0.0 |
| Vitamin A Palmitate | 0.0 | 0.05 | 0.0 | 0.0 | 0.0 | 0.0 | 0.0 |
| L. | | | | | | | |
| Aloe Vera Gel | 0.0 | 0.0 | 3.0 | 0.0 | 0.0 | 0.0 | 0.0 |
| Chamomile Extract | 0.0 | 0.0 | 0.1 | 0.0 | 0.0 | 0.0 | 0.0 |

*Contains about 1% propylene glycol.

The various components listed in the Table have been segregated into groups, the constituents of each group being mixed together before being added to members of the remaining groups in accordance with the procedures set forth below.

In the first step, the mixture of components of phase A is stirred for approximately 5 minutes with sheer mixing until homogeneous. With high speed sheer mixing, the materials of phase B are added gradually to A and the batch is mixed for 20 minutes until dispersed.

The components of phase C and then phase D are slowly added to the mixture of phases A and B with high shear mixing until dispersed. Silica is added at this point and dispersed through the mixture.

The resulting batch heated to 90° C. before the addition of the components of phase E. The vessel is cooled to 55° C. and the premixed phase F is added. The batch is mixed until homogeneous. The mixture is cooled to 30° C. and phase G is added.

A premix of phase H is made by mixing all the components until completely dissolved. At 30° C. the premix of phase H is added to the batch mixture with high shear, ensuring that there is no excess water on the surface. The mixture is then milled for 15 minutes.

Finally phases I, J, K, and L are added as diluent.

The resulting make-up composition is ready for packaging.

The make-up compositions of the Examples exhibit anti-acne activity and improved formulation and colour stability.

We claim:

1. A cosmetic composition in the form of a water-in-oil or oil-in-water emulsion comprising:
   a.) from about 0.1% to about 10% by weight of an acidic anti-acne active selected from the group consisting of salicylic acid, retinoic acid, azelaic acid, lactic acid, glycolic acid, pyruvic acid, flavonoids, and mixtures thereof dissolved in the aqueous phase;
   b.) from about 0.1% to about 10% by weight of a pyrrolidone-based complexing agent;
   c.) from about 0.1 to about 25% by weight of a pigment or mixture of pigments dispersed in the oil phase;
   d.) from about 1% to about 50% by weight of silicone oil selected from the group consisting of volatile silicones, non-volatile silicones and mixtures thereof;
   e.) from about 0.1% to about 30% by weight of a humectant selected from the group consisting of sorbitol, propylene glycol, butylene glycol, hexylene glycol, glycerin, alkoxylated glucose derivatives, hexanetriol, glucose ethers, urea, D-panthenol, DL-panthenol, calcium pantothenate, royal jelly, panthetine, pantotheine, panthenyl ethyl ether, pangamic acid, pyridoxin, pantoyl lactose, vitamin B complex, polyglycerylmethacrylate lubricants having a viscosity of from about 300,000–1,100,000 cp at 25° C., and mixtures thereof;
   f.) from about 0.1% to about 10% by weight of a matte finishing agent selected from the group consisting of silica, hydrated silica, mica, talc, polyethylene, titanium dioxide, bentonite, hectorite, kaolin, chalk, diatomaceous earth, attapulgite, zinc oxide and mixtures thereof; and
   g.) from about 1% to about 15% by weight of an emollient which is a natural or synthetic oil selected from the group consisting of mineral oils, vegetable oils, animal oils) fats, waxes, fatty acid esters, fatty alcohols, alkylene glycol ethers, alkylene glycol esters, polyalkylene glycol ethers, polyalkylene glycol esters, fatty acids and mixtures thereof
wherein the pigment or mixture of pigments is treated with a material selected from the group consisting of silicones, lecithin, lauroyl, collagen, polyethylene, amino acids and ester oils.

2. A cosmetic composition according to claim 1 wherein the aqueous phase comprising the anti-acne active dissolved therein is an aqueous/alcoholic solution of the anti-acne active having a pH of less than about $pK_a+1$, where $pK_a$ is the logarithmic acidity constant for the fully protonated anti-acne active.

3. A make-up composition according to claim 2 wherein the pyrrolidone-based complexing agent is a polyvinylpyrrolidone complexing agent.

4. A cosmetic composition according to claim 1 wherein said anti-acne active is selected from the group consisting of salicylic acid and azelaic acid and mixtures thereof.

5. A cosmetic composition according to claim 1 additionally comprising from about 0.01% to about 5% by weight of citric acid or salt thereof.

6. A cosmetic composition according to claim 1 in the form of a water-in-oil emulsion.

7. A cosmetic composition according to claim 1 wherein the volatile silicone oil is selected from the group consisting of cyclic polyorganosiloxanes having viscosities of less than about 10 centistokes and linear polyorganosiloxanes having viscosities of less than about 5 centistokes at 25° C., and mixtures thereof.

8. A cosmetic composition according to claim 7, wherein the volatile silicone oil is selected from the group consisting of cyclic polydimethylsiloxanes having from 3 to 9 silicon and linear polydimethylsiloxanes having from 3 to 9 silicon atoms.

9. A cosmetic composition according to claim 1 wherein the non-volatile silicone oil comprises a polydiorganosiloxane-polyoxyalkylene copolymer containing at least one polydiorganosiloxane segment and at least one polyoxyalkylene segment.

10. A cosmetic composition according to claim 9 wherein the polydiorganosiloxane-polyoxyalkylene copolymer is dimethicone copolyol.

11. A cosmetic composition according to claim 1 wherein the humectant is glycerine.

12. A cosmetic composition according to claim 1 comprising from about 0.1% to about 5% by weight of anti-acne active.

13. A cosmetic composition according to claim 1 comprising from about 0.1% to about 5% by weight of pyrrolidone-based complexing agent.

14. A cosmetic composition according to claim 1 wherein the silicone oil comprises from about 2% to about 25% by weight of the composition of non-volatile silicones.

15. A cosmetic composition according to claim 1 comprising from about 5% to about 25% by weight of composition of humectant.

16. A cosmetic composition according to claim 1 wherein the cross-linked hydrophobic copolymer is in the form of a lattice and wherein at least one active ingredient is dispersed uniformly throughout and entrapped within the copolymer lattice, the active ingredient being selected from the group consisting of skin compatible oils, skin compatible humectants, emollients, moisturizing agents and sunscreens.

17. A cosmetic composition according to claim 1 wherein the matte finishing agent is selected from the group consisting of silica and hydrated silica.

18. A cosmetic composition according to claim 1 wherein the emollient is selected from the group consisting of isopropyl palmitate, isopropyl isostearate, dioctyl maleate, propylene glycol dicaprylate/propylene glycol dicaprate, caprylic triglyceride/capric triglyceride, squalane, mineral oil, cetearylisononanoate and lanolin alcohol, and mixtures thereof.

19. A cosmetic composition according to claim 1 wherein the oil phase comprises form about 0.1% to about 10% by weight of humectant on a composition basis.

20. A cosmetic composition according to claim 1 comprising from about 30% to about 95% by weight of the oil phase and from about 5% to about 70% by weight of the water phase.

21. A cosmetic composition according to claim 1 additionally comprising one or more ultraviolet absorbing agents.

* * * * *

UNITED STATES PATENT AND TRADEMARK OFFICE
CERTIFICATE OF CORRECTION

PATENT NO.   : 5,871,754  
DATED        : February 16, 1999  
INVENTOR(S)  : Briggs et al.

Page 1 of 1

It is certified that error appears in the above-identified patent and that said Letters Patent is hereby corrected as shown below:

Column 12,  
Line 15, should read

-- Azeleic acid    0.0    0.0    .0.0    0.0    0.0    0.0    5 --

Signed and Sealed this

Eighteenth Day of December, 2001

Attest:

JAMES E. ROGAN  
Director of the United States Patent and Trademark Office

Attesting Officer